United States Patent [19]

Auten et al.

[11] Patent Number: 5,618,492

[45] Date of Patent: Apr. 8, 1997

[54] PROCESS FOR STERILIZING ARTICLES AND PROVIDING STERILE STORAGE ENVIRONMENTS

[76] Inventors: Richard D. Auten, 5960 Rolling Oaks La., Cumming, Ga. 30130; Barbara L. Heyl, 401 Glenwood Ave., Atlanta, Ga. 30312

[21] Appl. No.: 583,695

[22] Filed: Jan. 5, 1996

Related U.S. Application Data

[63] Continuation of Ser. No. 294,517, Aug. 23, 1994, abandoned.

[51] Int. Cl.⁶ ..................................................... A61L 2/00
[52] U.S. Cl. ..................... 422/22; 250/455.11; 134/901; 422/24; 422/28; 422/40
[58] Field of Search ............................. 422/22, 24, 28, 422/40, 292, 297, 300, 301, 305; 250/495.11; 134/901; 53/111 R, 111 RC; 206/51, 270, 363, 438

[56] References Cited

U.S. PATENT DOCUMENTS

| | | | |
|---|---|---|---|
| 3,549,528 | 12/1970 | Armstrong | 210/60 |
| 3,704,096 | 11/1972 | Verses | 23/230 |
| 3,912,451 | 10/1975 | Gaglia, Jr. | 422/30 |
| 4,156,652 | 5/1979 | Wiest | 250/527 |
| 4,410,442 | 10/1983 | Lucas et al. | 252/107 |
| 4,609,471 | 9/1986 | Beemster et al. | 210/748 |
| 4,746,489 | 5/1988 | Arnold | 422/29 |
| 4,868,397 | 9/1989 | Tittel | 422/24 X |
| 4,899,057 | 2/1990 | Koji | 422/24 X |
| 4,988,484 | 1/1991 | Karlson | 422/186 |
| 5,082,558 | 1/1992 | Burris | 422/119 X |
| 5,120,499 | 6/1992 | Baron | 422/24 |
| 5,182,258 | 1/1993 | Chiou | 514/3 |
| 5,184,633 | 2/1993 | Langford | 135/5 TR |
| 5,213,759 | 5/1993 | Castberg et al. | 422/24 |

FOREIGN PATENT DOCUMENTS

| | | |
|---|---|---|
| 508837 | 1/1979 | Australia . |
| 170602 | 2/1986 | European Pat. Off. . |
| 222309 | 5/1987 | European Pat. Off. ........ B65B 55/10 |
| 441389 | 8/1991 | European Pat. Off. . |
| 3138215 | 2/1986 | Germany . |
| 1178518 | 9/1968 | United Kingdom . |
| 2239452 | 3/1991 | United Kingdom .............. C02F 9/00 |
| 93/06948 | 4/1993 | WIPO . |

*Primary Examiner*—Robert J. Warden
*Assistant Examiner*—Krisanne M. Thornton
*Attorney, Agent, or Firm*—Edward McC. Roberts; R. Scott Meece; Michael U. Lee

[57] ABSTRACT

A process for producing a sterile article in a sealed container during a continuous production process. In a preferred embodiment, a contact lens is immersed in an ozone-containing solution within a container during a continuous lens packaging process, and the lens and container are subsequently subjected to ultraviolet radiation. This process sterilizes the contact lens and lens container in order to maintain the contact lens in a sterile environment during shipping, handling, and storage.

17 Claims, No Drawings

PROCESS FOR STERILIZING ARTICLES AND PROVIDING STERILE STORAGE ENVIRONMENTS

This application is a continuation of application Ser. No. 08/294,517, filed on Aug. 23, 1994, now abandoned.

BACKGROUND OF THE INVENTION

1. FIELD OF THE INVENTION

This invention relates broadly to article sterilization and sterile article storage technologies. More specifically, this invention relates to the sterilization of ophthalmic lenses and lens storage containers during contact lens production or packaging processes.

2. DESCRIPTION OF THE RELATED ART

Disinfection and cleaning methods are essential to the contact lens field. The patient or contact lens consumer commonly performs the disinfection process using self-contained over-the-counter disinfection products. A wide variety of contact lens disinfection methods which are directed to over-the-counter products have been disclosed in the literature and in patents.

For example, the use of hydrogen peroxide to disinfect contact lenses is well known. The hydrogen peroxide is typically decomposed after lens disinfection by a catalyst, such as the platinum catalyst disclosed in U.S. Pat. No. 3,912,451, issued to Gaglia. One example of a highly successful commercial hydrogen peroxide-based disinfection system designed for over-the-counter sale is the AOSEPT® disinfectant, cup, and disc, produced by CIBA Vision Corporation. While a wide variety of other patents have issued in the area of hydrogen peroxide lens disinfecting processes, there exist other methods for user disinfection of contact lenses.

A number of other disinfection processes have been disclosed in the art. For example, the boiling of contact lenses has been employed as a consumer-used disinfection method. However, boiling requires electrical power, which is a serious disadvantage because of consumers' convenience concerns. Another consumer-operated lens disinfection method involves the use of ozone, a known bactericide.

For example, U.S. Pat. No. 4,746,489, issued to Arnold, discloses a device and method for consumer disinfection of contact lenses with ozone. The method involves producing ozone by ionization, causing the ozone to migrate across a filter membrane, and causing the ozone to diffuse into an isotonic solution for soaking the lenses. The lenses are soaked on the order of two hours in the Arnold device. The Arnold device and method are claimed to be advantageous over other consumer products in the simplicity and absence of undesirable side effects.

U.S. Pat. No. 5,082 558 issued to Burris, also discloses a device and method for consumer disinfection of contact lenses. The disinfection device includes a chamber for containing a contact lens submerged in a liquid, a generator for producing ozone gas, a liquid circulation passageway, an output gas passageway, and a pumping system. Liquid is circulated through a junction, through which ozone is passed. The ozonated liquid is passed across the contact lens, then recirculated through the junction to repeat the ozonation step. The Burris disclosure indicates that this consumer-operated device is useful in improving contact lens hygiene as compared to other traditional consumer-operated disinfection methods.

With respect to sterilization processes useful in a manufacturing setting, European Patent Application No. 0 222 309 A1 discloses a process using ozone in which packaging material is disinfected. The process involves feeding an oxygen stream into an ozonating chamber, generating ozone from oxygen in the ozonating chamber, placing packaging containers in a sanitizing chamber, feeding the ozone into the sanitizing chamber, and purging the ozone from the sanitizing chamber with sterile air. The process requires that the ozone contact the packaging material for a predetermined time, followed by the sterile air purge step. The process is offered as an alternative to hot-sterilization, sterilization by application of electromagnetic radiation, or chemical agent sterilization.

Commercial contact lens manufacturing sterilization processes typically involve some form of temperature and/or pressure-based sterilization technique. For example, a hydrophilic contact lens is typically first formed by injecting a monomer mixture into a mold. The monomer mixture is then polymerized (i.e., the lenses are cured) by placing the mold in an oven over an extended time period. After other optional processing steps, such as quality inspections, the lens is placed in a container with a saline solution, and the container is sealed. The packaged lens is sterilized by placing the package in an autoclave at an elevated temperature and pressure for an extended period of time. Although this commercial process produces thoroughly sterilized contact lenses, the batch-wise autoclave sterilization step is time consuming and inefficient.

Although numerous consumer-oriented sterilization processes have been disclosed, there remains a need for a time-efficient, continuous, in-line production sterilization process. In addition, there is a need for a means of maintaining pharmaceutical, medical, and cosmetic products in a sterile environment during storage, absent the disadvantages associated with chemical additives.

SUMMARY OF THE INVENTION

An object of the invention is to provide a method of continuous sterilization of medical or cosmetic articles, especially contact lenses.

Another object of the invention is to provide an efficient method of producing sterile contact lenses in a continuous fashion.

Yet another object of this invention is to provide a method of providing a sterile environment for contact lenses for extended storage, shipping, or handling periods.

A further object of the invention is to reduce the time required to sterilize contact lenses in a lens production process.

Another object of this invention is to provide a method of chemical sterilization of articles without damage to the article or package material.

One embodiment of the present invention is a method of sterilizing articles in a continuous fashion during the packaging of the article. The sterilization method involves immersing the article in an ozonated solution retained by a container, followed by sealing the container. In one embodiment, the ozone concentration of the solution alone is sufficient to sterilize the article over the time period of contact. In a preferred embodiment, sterilization is accomplished by a combination of contact with ozone and application of ultraviolet light. Preferably, the article is a hydrophilic contact lens and the solution is an ozonated, buffered isotonic saline solution.

In another embodiment of the present invention, the ozone in the sterilization solution is degraded prior to shipment of the article to sales and marketing sites. Accelerated ozone degradation may be caused by application of a predetermined intensity of ultraviolet light or heat to the package containing the article and ozonated sterilization solution. Further, agitation of the package may accelerate the ozone degradation. A combination of application of heat, light, and/or agitation may be applied to the package to prematurely degrade the ozone.

DESCRIPTION OF THE PREFERRED EMBODIMENTS

The present invention is a method of sterilizing articles and article storage containers during a continuous production process. In one embodiment, the invention is useful in preparing sterile containers for housing devices or materials formed in whole or in part from hydrogels. In another embodiment, the invention may be utilized to produce sterile packages for shipping and storing medical devices, such as surgical instruments. However, the invention offers special utility in the preparation of sterile contact lenses and sterile protective packages for retaining contact lenses during shipping, storage, or other handling. Accordingly, the invention will be described in reference to the preferred contact lens sterilization process.

Contact lenses can be advantageously sterilized in accordance with the present invention by immersing the lenses in a solution containing a predetermined concentration of ozone for a time sufficient to sterilize the lenses. The process of sterilization may be incorporated in-line into a continuous contact lens production process. In a preferred embodiment, the sterilization process is applied to a hydrophilic (i.e., soft) contact lens production process.

Hydrophilic contact lens production processes include a first step of lens formation. This step typically includes preparation of a monomer mixture, injection of the monomer mixture into a mold, and polymerization or curing of the monomer mixture. Subsequent to the lens formation step, and prior to, but more commonly subsequent to, the lens packaging step, the traditional contact lens production process includes a sterilization step requiring increased temperature and pressure. Advantageously, according to the present invention, temperature and/or pressure-based sterilization steps (e.g., autoclave sterilization) may be eliminated.

In order to maximize process efficiency, the present sterilization process is incorporated into a contact lens production and packaging process as a continuous step. In a preferred embodiment, the sterilization step is incorporated into the lens packaging step. In many commercial lens packaging processes, the lens and a saline solution are placed into a container, and a liquid impermeable seal is formed on the container. This sealed container is then prepared, and possibly further packaged, for shipping and storage. In accordance with one embodiment of the present invention, the sterilization is achieved by incorporating ozone into the saline solution into which the lenses are typically immersed when placed in the sealed storage container. By incorporating ozone into the saline storage solution, and thereby avoiding a separate sterilization step, the present invention reduces processing time as compared with prior art heat sterilization processes.

In another embodiment, the ozone is degraded just prior to completion of the packaging process. The ozone may be degraded by application of light, heat, and/or mechanical agitation. Preferably, ultraviolet (UV) light is applied to the sealed lens package prior to distribution from the production facility. application of UV light is preferred because the UV light not only degrades the ozone, but also further sterilizes the contact lens and lens container. Thus, UV light is applied at an intensity and over a time period sufficient to substantially degrade the ozone into harmless dissolved diatomic oxygen, and to provide any required additional sterilization of the lens and container. In this embodiment, any possible adverse effect of dissolved ozone is eliminated prior to distribution of the product to the consumer. In addition, UV light aids in killing or deactivating certain forms of bacteria, thereby further insuring a complete sterilization. The ultraviolet light may be applied at an intensity of about 0.25 $J/cm^2$ to about 20 $J/cm^2$ over a period of about 15 seconds to about 20 minutes, more preferably at an intensity of about 5 $J/cm^2$ to about 10 $J/cm^2$ over a period of about one to about ten minutes.

The sterilization solution is preferably an isotonic saline solution having ozone dissolved therein. The amount of dissolved ozone must be sufficient to completely sterilize the contact lens and storage package. The bactericidal effect of the ozonated sterilization solution is dependent on ozone concentration, contact time, and bioburden. Typically, the lens contact time with the storage solution may range from about one minute to about 30 minutes. In a preferred embodiment, the article is both contacted with ozonated solution and irridated with UV radiation. Preferably, the article is contacted with the sterilization solution, including dissolved ozone, for a period of one to 15 minutes, more preferably for a period of one to three minutes. Preferably, the ozonated solution, in combination with applied UV light, will kill or deactivate substantially all bacteria within about one to about 15 minutes, more preferably about one to about 3 minutes, of lens contact therewith. Preferably, the concentration of ozone is the saturation concentration for the sterilization solution, which is about 30 parts per million (ppm). However, the concentration of ozone in the storage solution may range from about 1 to about 30 ppm. More preferably, the concentration ranges from about 5 to about 30 ppm. The most preferred ozone concentration is above about 10 ppm.

There are numerous methods of dissolving ozone into the lens storage solution. Preferably, an ozone-containing gas stream is contacted with the storage solution at conditions sufficient to generate mixing between the solution and the ozone stream. Agitation enhances the mass transfer of ozone from the gas phase into the liquid phase of the storage solution. Thus, for example, an ozone-containing gas! stream and a storage solution stream may be passed through sintered glass, through a venturi, through a static motionless mixer, or through another orifice designed to increase agitation, turbulence or mix two streams.

Also, the temperature of the storage solution is preferably reduced to below about 20° C., more preferably to about 0° to 10° C., and maintained at this reduced temperature. Generally, the lower the temperature of solution, the higher the concentration of ozone that may be dissolved therein.

As mentioned previously, the ozonated sterilization and storage solution is preferably an isotonic saline solution. Preferably, the saline solution includes about 0.8 to about 1.0 weight percent sodium chloride in water. In addition, the saline solution is preferably buffered to a pH of about 6.5 to about 7.5, in order to approximate the pH of the eye fluids. The solution may be buffered by a wide variety of buffers, including without limitation, phosphates, borates, citrates, and other biocompatible buffers known to those skilled in the art. However, the buffering is preferably accomplished by a phosphate, such as mono- and dibasic sodium phosphates, in an amount form about 0.5 to about 10 grams per liter. A preferred composition includes about 5 to 10 (preferably 8 to 9) g/L sodium chloride, ozone in an amount from about 10 ppm to saturation-level, 5 to 10 (preferably 7.5 to 8.5) g/L sodium chloride, about 0.5 to 1.0 (preferably 0.7 to 0.8) g/L sodium dihydrogen phosphate hydrate, about 3 to 7 (preferably about 4 to 5) g/L disodium hydrogen phosphate heptahydrate, and the balance water. The ozonated saline solution may contain a variety of other components which do not substantially harm the contact lens or the bactericidal character of the solution, such as dyes, surfactants, and the like.

Thus, in a preferred embodiment, a production lens and lens package sterilization process can be achieved by injecting an ozonated storage solution (e.g., phosphate-buffered saline solution) into a storage container in a substantially continuous fashion. The lens may be placed into the container either before or after the ozonated storage solution is injected into the container. Subsequent to sealing the container, after a predetermined contact time, the lens package may be exposed to UV light at an intensity and over a period of time sufficient to substantially degrade the ozone to dissolved oxygen and to provide any desired additional sterilization.

In another embodiment, a lens and storage solution may first be placed into a storage container. Then, an ozone stream may be passed through the storage solution while the solution is in the storage container, thereby dissolving ozone into the solution. This process has advantages in increasing agitation within the container, thereby enhancing ozone contact with any microorganisms which may be present.

The contact lenses useful in accordance with the present invention may be formed by a number of processes and formed from a number of materials. For example, the lenses may be hydrophilic lenses formed from the polymerization or copolymerization of acrylates or methacrylates, such as 2-hydroxyethyl methacrylate (i.e., HEMA); hydrophobic lenses formed from polysiloxanes; or lenses formed from copolymers displaying a range of hydrophobic and hydrophilic properties. However, the sterilization process disclosed herein is not limited by the selection of the article to be sterilized.

The previous disclosure will enable one having ordinary skill in the art to practice the invention. In order to better enable the reader to understand specific embodiments and the advantages thereof, reference to the following examples is suggested.

EXAMPLE I

A gaseous ozone stream containing about one to about three weight percent ozone, with the balance oxygen, is prepared. The gaseous ozone stream is passed through a glass sparger into a phosphate-buffered saline solution (mono- and dibasic sodium phosphates in an amount sufficient to maintain a pH of about 7). The resulting buffered, ozonated solution contains absorbed ozone at a concentration of about 3 to 6 ppm, as measured by a Griffin Technics dissolved-ozone meter.

Approximately 20 ml samples of buffered, ozonated solution are placed in three Falcon tubes. The three Falcon tubes are inoculated with approximately $10^6$ *Seratia marcescens*, *Psuedomonas aeruginosa*, and *Aspergillus fumigatus*, respectively. After 2, 5, 10, 20 and 30 minute periods of contact with the ozone solution, one ml aliquots of each of the Falcon tube solutions are removed. These 1 ml samples are placed in 9 ml aliquots of Dey Engley broth, and then serially diluted, plated, and incubated.

TABLE 1 shows the surviving number of organisms as a function of contact time with the buffered ozone solution and type of organism.

TABLE 1

| Organism | 0 min. | 2 min. | 5 min. | 10 min. | 20 min. | 30 min. |
|---|---|---|---|---|---|---|
| S. marcescens | $10^1$ | <20 | <20 | <20 | <20 | <20 |
| P. aeruginosa | $10^3$ | $10^1$ | <20 | <20 | <20 | <20 |
| A. fumigatus | $10^6$ | $10^6$ | $10^6$ | $10^6$ | $10^6$ | $10^6$ |

A total kill, i.e. values below detectable limits (<20), of both *S. marcescens* and *P. aeruginosa* occurs in less than 5 minutes. However, *A. fumigatus* survives this buffered, ozonated solution treatment.

EXAMPLE II

A gaseous ozone stream containing about one to about three weight percent ozone is prepared. The gaseous ozone stream and a phosphate-buffered saline solution are passed through a venturi injector in order to thoroughly mix the streams and maximize the dissolved ozone concentration. The resulting buffered, ozonated solution contains absorbed ozone at a concentration of about 4 to 10 ppm, as measured by the spectrophotometric indigo method (See Standard Methods for the Examination Of Water and Wastewater, 17th Ed. (1989)).

A sample of buffered, ozonated solution, about 20 ml, is placed in a Falcon tube. The Falcon tube is inoculated with approximately $10^6$ *Aspergillus fumigatus*. After a 10 minute contact period with the ozone solution, a one ml aliquot of the Falcon tube solution is removed. This one ml samples is placed in a nine ml aliquot of Dey Engley broth, and then serially diluted, plated, and incubated.

A 10 minute contact time with ozonated solution prepared substantially as described in Example II causes a 2.2 logarithmic drop in concentration of *Aspergillus fumigatus*.

EXAMPLE III

A gaseous ozone stream containing about one to about three weight percent ozone is prepared. The gaseous ozone stream and a phosphate-buffered saline solution are passed through a venturi injector in order to thoroughly mix the streams and maximize the dissolved ozone concentration. The resulting buffered, ozonated solution contains absorbed ozone at a concentration of about 4 to 10 ppm, as measured by the spectrophotometric indigo method.

A sample of buffered, ozonated solution, about 20 ml, is placed in a Falcon tube. The Falcon tube is inoculated with approximately $10^6$ *Aspergillus fumigatus*. After a 10 minute contact period with the ozone solution, the sample is treated with ultraviolet light at an intensity of about 1.2 J/cm$^2$ for about a two minute period. Then, a one ml aliquot of the Falcon tube solution is removed. This one ml sample is placed in a nine ml aliquot of Dey Engley broth, and then serially diluted, plated, and incubated.

A 10 minute contact time with ozonated solution prepared substantially as described in Example III, followed by about a two minute UV light treatment substantially as described in Example III, yields a 3.6 logarithmic drop in concentration of Aspergillus fumigatus.

EXAMPLE IV

A gaseous ozone stream containing about one to about three weight percent ozone and a USP water stream, cooled to a temperature of about 5° to 10° C., are prepared. Then, the gaseous ozone stream and the cooled water stream are passed through a venturi injector in order to thoroughly mix the streams and maximize the dissolved ozone concentration. The resulting ozonated solution contains absorbed ozone at a concentration of about 10 to 20 ppm, as measured by the spectrophotometric indigo method.

A sample of the ozonated solution, about 20 ml, is placed in a Falcon tube. The Falcon tube is inoculated with approximately $10^6$ *Aspergillus fumigatus*. After a 10 minute contact period with the ozone solution, a one ml aliquot of the Falcon tube solution is removed. This one ml sample is placed in a nine ml aliquot of Dey Engley broth, and then serially diluted, plated, and incubated.

A 10 minute contact time with ozonated solution prepared substantially as described in Example IV yields an *Aspergillus fumigatus* concentration below detectable limits. Thus, the treatment of a contact lens with 10-20 ppm ozone solution for a period of about 10 minutes is sufficient to kill or deactivate substantially all problematic microorganisms, i.e., S. marcescens and P. aeruginosa, and A. fumigatus.

EXAMPLE V

A continuous contact lens packaging process is provided with an in-line lens and lens package sterilization process in the following manner.

A substantially isotonic saline solution buffered to a pH of about 7 is provided. The saline solution is cooled to a temperature of about 5° to 10° C. and maintained at that temperature. A gaseous stream containing about one to three weight percent ozone is passed through the cooled saline solution at a rate sufficient to create and maintain the concentration of dissolved ozone in the solution at about 10 to 20 ppm.

Contact lenses are placed in lens storage packages in a substantially continuous fashion. Ozonated saline solution is poured into the lens container in an amount sufficient to substantially immerse the contact lens contained therein. The lens package is provided with a liquid-impermeable seal.

EXAMPLE VI

The lens packages are prepared substantially as described in Example V. After 10 minutes of contact with the ozonated solution, the lens packages are treated with ultraviolet light at an intensity of about 10 J/cm² for about 2 minutes. The ultraviolet light provides added antimicrobial value, while stimulating the conversion of the dissolved ozone into dissolved oxygen.

The invention has been described in detail, with reference to certain preferred embodiments, in order to enable the reader to practice the invention without undue experimentation. However, a person having ordinary skill in the art will readily recognize that many of the previous components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, the intellectual property rights to this invention are defined only by the following claims.

That which is claimed is:

1. A method of sterilizing an article and providing a sterile storage container for an article, comprising the steps of:
   (a) providing a sterilization solution including ozone dissolved therein;
   (b) placing said sterilization solution in a container;
   (c) placing an article to be sterilized in said container;
   (d) sealing said container, thereby allowing said article to become at least partially immersed in said sterilization solution for a predetermined time, wherein said predetermined contact time is less than about 30 minutes; and
   (e) applying ultraviolet radiation to said container after a predetermined contact time with said sterilization solution, wherein said contact time with ozone and ultraviolet radiation is a time sufficient to simultaneously sterilize said article and wherein said ultraviolet light degrades said ozone.

2. A method of claim 1, wherein said article is selected from the group consisting of medical, optical and ophthalmic devices.

3. A method of claim 2, wherein said article is a contact lens.

4. A method of claim 1, wherein said solution is a substantially isotonic saline solution.

5. A method of claim 4, wherein said solution further comprises a buffer in an amount sufficient to maintain solution pH between 6.5 and 7.5.

6. A method of claim 5, wherein said buffer includes monobasic sodium phosphate and dibasic sodium phosphate.

7. A method of claim 1, wherein the concentration of ozone in said solution is between about one ppm and the saturation level of the solution.

8. A method of claim 7, wherein the concentration of ozone in said solution is between about 10 ppm and 30 ppm.

9. A method of claim 1, wherein said solution further comprises sodium chloride in an amount sufficient to form a substantially isotonic solution.

10. A method of claim 9, wherein said sodium chloride concentration is about 0.8 to about 1.0 weight percent.

11. A method of claim 1, wherein said ultraviolet radiation is applied at an intensity of 0.25 J/cm² to 20 J/cm² for a period of between 15 seconds and 20 minutes.

12. A method of claim 11, wherein said ultraviolet radiation is applied at an intensity of 5 J/cm² to 10 J/cm² for a period of between one and 10 minutes.

13. A method of claim 1, wherein said solution is held at a temperature of about 0° C. to about 10° C. during said predetermined contact time.

14. A method of claim 1, wherein said predetermined contact time is about one to about 15 minutes.

15. A method of claim 14, wherein said predetermined contact period is about one to about three minutes.

16. A method of producing sterile contact lens packages in a continuous fashion, comprising the steps of:
   (a) forming a hydrophilic lens;
   (b) placing said lens and a solution including ozone dissolved therein in a container
   (c) applying ultraviolet radiation to said container after a predetermined contact time with said sterilization solution, wherein said contact time with said ozone and said ultraviolet radiation is a time sufficient to simultaneously sterilize said lens, and wherein said ultraviolet light degrades said ozone; and
   (d) sealing said container, thereby maintaining said lens in a sterile environment until said sealed container is opened.

17. A method of claim 16, further comprising the step of applying ultraviolet radiation to said container holding said contact lens, wherein said ultraviolet radiation simultaneously sterilizes said lens and degrades said ozone.

\* \* \* \* \*